United States Patent [19]

Michael et al.

[11] Patent Number: 4,650,893

[45] Date of Patent: Mar. 17, 1987

[54] BIS-IMIDO CARBONATE SULPHONES

[75] Inventors: Jeffrey D. Michael, Milton Keynes; Barry C. Ross, Luton, both of England

[73] Assignee: Hoechst UK Limited, England

[21] Appl. No.: 753,890

[22] Filed: Jul. 10, 1985

[30] Foreign Application Priority Data

Jul. 31, 1984 [GB] United Kingdom ............... 8419460

[51] Int. Cl.$^4$ ........................................... C07C 119/20
[52] U.S. Cl. ........................................ 558/6; 564/79; 544/7
[58] Field of Search ................... 260/453.8, 453.99; 564/79; 558/6

[56] References Cited

U.S. PATENT DOCUMENTS 4,293,454 10/1981 Monsimer et al. ............... 564/79
4,490,306 12/1984 Acker ............................ 564/79

Primary Examiner—John M. Ford
Attorney, Agent, or Firm—Finnegan, Henderson, Farabow, Garrett & Dunner

[57] ABSTRACT

Bis-imido carbonate sulphones of the formula:

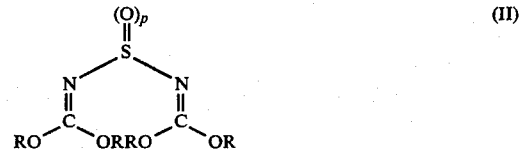

in which R represents phenyl which is unsubstituted or substituted by one or two substituents, which is the same or different, selected from methyl, trifluoromethyl, nitro and cyano groups, and chlorine, flourine and bromine atoms, and p represents the integer 1, are produced by reacting a compound of formula VI

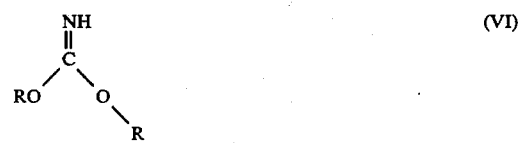

in which R is as defined above, with thionyl chloride in the presence of an organic base. The compounds of formula II are useful in the production of 1, 2, 4, 6-thiatriazines.

3 Claims, No Drawings

BIS-IMIDO CARBONATE SULPHONES

The present invention relates to a process for the production of 4-substituted 1,2,4,6-thiatriazine derivatives which are useful, inter alia, in the production of compounds having histamine $H_2$-antagonist activity, and also relates to certain of the 4-substituted 1,2,4,6-thiatriazine derivatives per se.

Our UK Patent Specification No. 2 129 426A describes and claims thiatriazine derivatives that have histamine $H_2$-antagonist activity and that are useful in the treatment of gastric hyperacidity and gastric ulcers, and also describes and claims processes for the production of these compounds. These processes utilise certain 4-substituted 1,2,4,6-thiatriazine 1,1-dioxides.

The present invention provides a process for the production of a compound of formula I

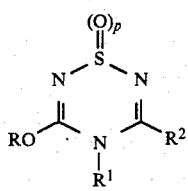
(I)

in which

R represents an aryl group, which may be unsubstituted or substituted by one or two substituents, which may be the same or different, selected from methyl, trifluoromethyl, nitro and cyano groups, and chlorine, fluorine and bromine atoms;

$R^1$ represents a hydrogen atom, a straight or branched chain alkyl group having from 1 to 6 carbon atoms or a cycloalkyl group having from 3 to 7 carbon atoms, which alkyl or cycloalkyl group is unsubstituted or is substituted by one or more substituents, which may be the same or different, for example, by one or two substituents, especially by one substituent, selected from halogen atoms; nitro and cyano groups; —$OR^4$ groups in which $R^4$ represents a hydrogen atom or an alkyl group having from 1 to 4 carbon atoms; cycloalkyl groups having from 3 to 7 carbon atoms; $NR^5R^6$ groups in which $R^5$ and $R^6$, which may be the same or different, each represents a hydrogen atom or an alkyl group having from 1 to 4 carbon atoms; —$COOR^7$ groups in which $R^7$ represents a hydrogen atom or a carboxylic acid esterifying group; group; —$CONR^5R^6$ groups in which $R^5$ and $R^6$ are as defined above; —$SO_2NR^5R^6$ groups in which $R^5$ and $R^6$ are as defined above; aromatic and non-aromatic heterocyclic groups having from 5 to 8 ring members and 1 or 2 heteroatoms, which may be the same or different, selected from oxygen, nitrogen and sulphur atoms and optionally having an alkyl group having from 1 to 4 carbon atoms as a substituent on a ring nitrogen atom; and phenyl groups $R^8$ that are unsubstituted or substituted by one or more substituents, which may be the same or different, selected from halogen atoms, trifluoromethyl groups, nitro and cyano groups, alkyl and alkoxy groups having from 1 to 4 carbon atoms, and $NR^5R^6$ groups in which $R^5$ and $R^6$ are as defined above; or $R^1$ represents a straight or branched chain alkenyl group having from 2 to 6 carbon atoms or a straight or branched chain alkynyl group having from 3 to 6 carbon atoms;

$R^2$ represents an aryloxy group which is unsubstituted or is substituted as defined above for aryl groups R; or $R^2$ represents an —$NHR^3$ group in which $R^3$ represents a hydrogen atom, a straight or branched chain alkyl group having from 1 to 6 carbon atoms that is unsubstituted or is substituted as defined above for alkyl groups $R^1$, or an aromatic or non-aromatic heterocyclic group as defined above; or $R^2$ represents a group $NHR^3$, and $R^1$ and $R^3$, together with the atoms to which they are attached, form a 5- or 6-membered ring containing two nitrogen atoms, and p represents the integer 1 or 2, which comprises (a) reacting a compound of formula II

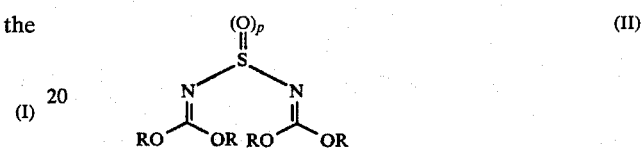
(II)

in which R and p are as defined above, with an amine of formula III $R^1$—$NH_2$ (III)

in which $R^1$ is as defined above to give a compound of Formula Ia

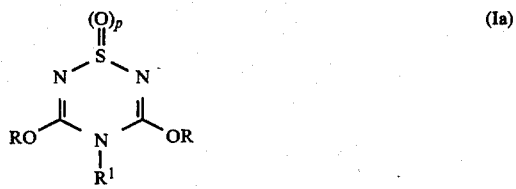
(Ia)

in which R, p and $R^1$ is as defined above, that is to say, a compound of formula I in which $R^2$ represents an optionally substituted aryloxy group and, if desired, (b) reacting the resulting compound of formula Ia with an amine of formula IV $R^3$—$NH_2$ (IV)

in which $R^3$ is as defined above, to give a compound of Ib

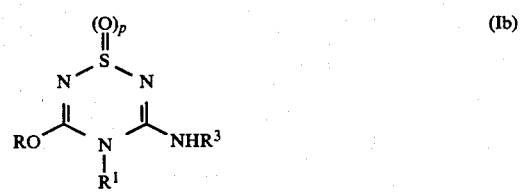
(Ib)

in which R, p, $R^1$ and $R^3$ are as defined above, that is to say, a compound of formula I in which $R^2$ represents a group —$NHR^3$; or (c) reacting a compound of formula II as defined above with a diamine of formula V $H_2N$—$(CH_2)_n$—$NH_2$ (V)

in which n represents 2 or 3 to give a compound of formula

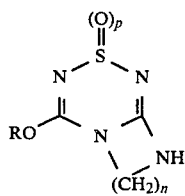

(Ic)

in which R, p and n are as defined above, that is to say, a compound of formula I in which $R^2$ represents a group $NHR^3$, and $R^1$ and $R^3$, together with the atoms to which they are attached, form a 5- or 6-membered ring containing two nitrogen atoms; and, if desired, at any stage, (d) oxidising a resulting compound of formula I in which p represents the integer 1 to give the corresponding compound in which p represents the integer 2.

The term "aryl" is used herein to denote a radical derived from benzene or from a polynuclear arene, for example, derived from diphenylmethane or naphthalene (see Roberts and Caserio, Basic Principles of Organic Chemistry, W. A. Benjamin, Inc., New York, 1964). An aryl group is preferably a phenyl group. Carboxylic acid esterifying groups are well known, that is to say, in actual use in the art or described in the literature of the art. For carboxylic acid protecting groups see, for example, McOmie, Protecting Groups in Organic Chemistry, Plenum Press, London 1973, and Greene, Protecting Groups in Organic Synthesis, J. Wiley & Sons Inc. 1981.

In a compound of formula I, an aromatic or non-aromatic group is, for example, a furyl, tetrahydrofuryl, thienyl, pyridyl, dihydropyranyl, pyrrolidinyl, N-alkylpyrrolidinyl or piperidyl group, especially a furyl or pyridyl group. An alkyl substituent on a ring nitrogen atom is especially a methyl group.

The oxidation of a sulphoxide of formula I to the corresponding sulphone may be carried out by means of an oxidising agent, for example, a peracid, for example, peracetic acid or m-chloroperbenzoic acid; hydrogen peroxide; an alkylhydroperoxide, for example, t-butyl hydroperoxide; a permanganate, for example, potassium permanganate; or a perborate, for example, sodium perborate. The oxidation is carried out in a suitable solvent of diluent. A sulphoxide of formula Ia may be oxidised before reaction with the amine of formula III, or after formation of a compound of formula Ib.

Compound II is preferably reacted with the amine of formula III in a solvent or diluent, for example, an aprotic solvent or diluent that does not react with the amine III, for example, acetonitrile, dichloromethane, dioxane or tetrahydrofuran. Generally the reaction is carried out at a temperature within the range of from 0° to 100° C., preferably from 20° to 80° C., depending on the nature of any substituent(s) on the phenyl rings. Generally one mole of the amine is used per mole of compound II.

The reaction of a compound of formula II with a diamine of formula V, that is to say, with 1,2-diaminoethane or 1,3-diaminopropane is generally carried out under the reaction conditions described above for the reaction of compounds II and III, and the reaction of compounds Ia and IV is also generally carried out under those conditions.

A compound of formula II in which p represents the integer 1 may be produced by reacting a compound of formula VI

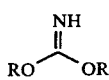

(VI)

in which R is as defined above, with thionyl chloride in the presence of an organic base, for example, a trialkylamine, for example, trimethylamine, triethylamine, or diethylisopropylamine. The reaction is generally carried out in a solvent or diluent, for example, an aprotic solvent, for example, acetonitrile, chloroform, dichloromethane, diethyl ether or tetrahydrofuran. The reaction temperature is generally within the range of from −50° to +30° C. A resulting compound of formula II in which p represents the integer 1 may be oxidised to give the corresponding compound of formula II in which p represents the integer 2 using reagents and reaction conditions as described above.

Many of the compounds of formula VI are unstable, giving triazines on standing, and must be prepared and then reacted immediately with thionyl chloride at low temperatures, for example, from −50° to −20° C. to prevent such a side reaction. A simple method for preparing diphenyl imidocarbonates of formula VI and observations on their instability are give by Nef in Annalen 287, 310 (1895).

Particularly useful compounds of formula VI are those in which the aryl groups R are phenyl groups and are each substituted by a methyl, trifluoromethyl, cyano or nitro group, or by a halogen atom, for example, a chlorine, bromine or fluorine atom, especially by a 2-nitro or 4-methyl group. When such a substituent is present, the reaction of a resulting compound of formula II (optionally after oxidation), with an amine of formula III or a diamine of formula V may be carried out at a lower temperature than is possible with the corresponding unsubstituted compound II. A subsequent reaction of a resulting compound Ia with an amine of formula IV is also facilitated by the presence of a halogen, trifluoromethyl, cyano or nitro (especially 2-nitro) substituent on the phenyl ring R. The presence of a halogen, trifluoromethyl, nitro or cyano substitutent, especially a 2-nitro substitutent, is particularly advantageous when a compound of formula II or Ia is to be reacted with a sterically hindered amine, for example, iso-propylamine or t-butylamine.

Accordingly, preferred compounds of formulae II are those in which each radical R represents a halogenophenyl, trifluoromethylphenyl, cyanophenyl, methylphenyl or nitrophenyl group, and especially those in which each radical R represents a 2-nitrophenyl or 4-methylphenyl group.

The process of the present invention is suitable for large-scale manufacturing use. The starting materials and reagents are readily available and inexpensive and, in general, the intermediate tetraphenyl-bis-imidocarbonate sulphoxides and sulphones of formula II are stable, highly crystalline compounds and as such are easily isolated from reaction mixtures without the need for chromatography.

Moreover, as described above, the reactivity of the displaceable phenoxy groups RO— can be controlled by careful selection of the phenyl ring substituents, thus increasing the versatility of the process of the invention to include the use of sterically hindered amines and diamines in the production of a compound of formula I.

In a resulting compound of formula I as in the intermediates described above, the reactivity of the displaceable phenoxy group RO— can be controlled by the selection and positioning of substituents on the phenyl ring. If two substituents are present on a phenyl ring, these are preferably in the 2- and 4-positions. Generally, it is preferable to have only one substituent. As mentioned above, a nitro group is preferably in the 2-position, and a methyl substituent is preferably in the 4-position. A particularly useful compound of formula I is 3,5-bis-(4-methylphenoxy)-4-methyl-1,2,4,6-thiatriazine 1,1-dioxide.

A compound of formula I produced by the process of the present invention may be used to produce a compound of formula VII $$A-(CH_2)_n-X-(CH_2)_m-NH-\underset{\underset{R^1}{N}}{\overset{O\ \ O}{\underset{\|}{\overset{\|}{S}}}}\underset{N}{\overset{N}{\diagdown}}R^2 \qquad (VII)$$

in which
A represents a phenyl, imidazolyl, thiazolyl, furyl, thienyl, or pyridyl radical, which radical may have one or two substitutents, selected from $(C_1-C_4)$alkyl, guanidino, and $-CH_2NR^9 R^{10}$ groups, $R^9$ and $R^{10}$, which may be the same or different, each representing a hydrogen atom or a $(C_1-C_6)$alkyl group, or together with the nitrogen atom to which they are attached, may form a pyrrolidine, piperidine, morpholine, or N-methylpiperazine ring;

X represents —O— or —S—;
n represents 0 or 1;
m represents 2 or 3; and
$R^1$ and $R^2$ are as defined above, by a process which comprises (a) reacting a compound of formula I as defined above with a compound of formula VIII $$A-(CH_2)_n-X-(CH_2)_m-NH_2 \qquad (VIII)$$

in which A, X, m and n are as defined above and, if desired, when $R^2$ in a resulting compound VII represents an aryloxy group, reacting that compound VII with an amine of formula IV $$H_2NR^3 \qquad (IV)$$

in which $R^3$ is as defined above to obtain a compound of formula VII in which $R^2$ represents an $-NHR^3$ group, or (b) reacting a compound of formula I obtained in accordance with the present invention with a compound of formula IX $$HX-(CH_2)_m-NH_2 \qquad (IX)$$

in which X and m are as defined above and reacting the resulting compound of formula X $$HX-(CH_2)_m-NH-\underset{\underset{R^1}{N}}{\overset{(O)_p}{\underset{\|}{\overset{\|}{S}}}}\underset{N}{\overset{N}{\diagdown}}R^2 \qquad (X)$$

with a compound of formula XI $$A-(CH_2)_n-L \qquad (XI)$$

in which A is as defined above and L represents a leaving group, for example, a halogen atom, a hydroxy group, an alkoxy group or a sulphonate ester.

The present invention includes such use of a compound of formula I.

Further details of this process and of compounds that may be prepared by this process are given in our UK Specification No. 2 129 426A.

Other substituted thiatriazines analogous to compound VII but having different side chains attached to the 5-position of the thiatriazine ring may be prepared analogously to compound VII. An example of such a compound is as defined above for compound VII but having as radical A a thiazolyl radical that is substituted by a guanidino group that is itself substituted by one or more alkyl groups, wherein the or each alkyl group may itself be substituted, for example, by a trifluoromethyl group or by a halogen atom.

In particular, the present invention provides the use of a compound of formula I (when produced by the process of the present invention) in the manufacture of a compound of formula XII $$\underset{NH_2}{\overset{NH_2}{\diagdown}}=N-\underset{N}{\overset{S}{\diagup\diagdown}}-CH_2-S-(CH_2)_2-NH-\underset{\underset{CH_3}{N}}{\overset{O\ \ O}{\underset{\|}{\overset{\|}{S}}}}\underset{N}{\overset{N}{\diagdown}}NH_2 \qquad (XII)$$

that is to say, 3-N-[(2-guanidino-4-thiazolyl)methylthio]ethyl]amino-4-methyl -5-amino-1,2,4,6-thiatriazine 1,1-dioxide.

The compound of formula XII may be produced by a process which comprises
(i) reacting a compound of formula XIII obtained by the process of the present invention $$RO-\underset{\underset{CH_3}{N}}{\overset{O\ \ O}{\underset{\|}{\overset{\|}{S}}}}\underset{N}{\overset{N}{\diagdown}}NH_2 \qquad (XIII)$$

in which compound R is defined as above, with a compound of formula XIV

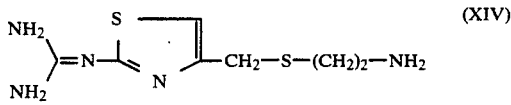

or (ii) reacting a compound of formula XV obtained by the process of the present invention

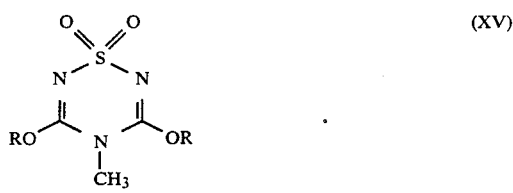

with a compound of formula XIV as defined above, and reacting the resulting compound of formula XVI

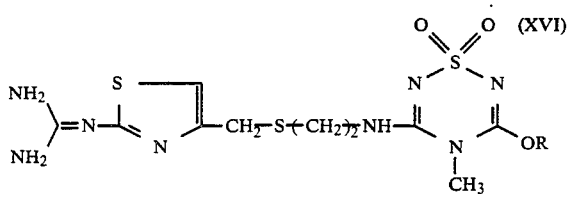

with ammonia, or (iii) reacting a compound of formula I obtained by the process of the present invention with an amino thiol of formula XVII

and reacting the resulting compound of formula XVIII

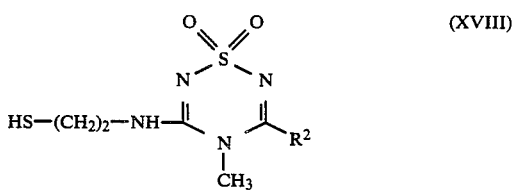

with a compound of formula XIX

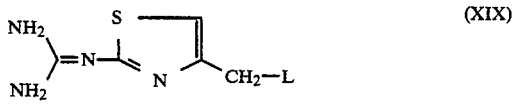

in which L represents a leaving group, for example, a halogen atom, a hydroxy group, an alkoxy group or a sulphonate ester.

Compounds XIII and XIV are generally reacted in a solvent or diluent, preferably an alcohol, dimethylformamide or dimethyl sulphoxide, at a temperature within the range of from 0° to 100° C., preferably from 0° to 60° C. The compound of formula XIV should be reacted in the form of the free base, as shown. If it is initially present in the form of an acid addition salt, for example, as the hydrochloride or hydrobromide, this should be converted into the free base during or, preferably, before reaction with compound XIII. Conversion to the free base is carried out using a base, for example, triethylamine, sodium hydroxide or potassium hydroxide.

Compound XV is reacted with compound XIV under conditions similar to those described above for the reaction of compounds XIII and XIV, except that generally lower temperatures are preferred in order that the groups RO— may be displaced selectively.

The reaction of the resulting compound XVI with ammonia is generally carried out in an alcoholic solvent at a temperature from 0° to 60° C.

In all cases, the group RO— in the thiatriazine starting material used for the production of compounds VII, XII and analogous compounds is preferably one of the substituted phenyl groups described above, in particular a 2-nitrophenyl group or a 4-methylphenyl group.

A number of compounds of formula XI are known, see for example, UK Specification No. 2 001 624A; U.S. Pat. No. 3,950,333; U.S. Pat. No. 4,128,658; and Belgian Pat. Nos. 867 106 and 875 846. Others may be prepared analogously. The preparation of compound XIV is described in UK Specification No. 2 001 624A.

Compounds of formula I as defined above find application as herbicides, and the present invention provides the use of a compound of formula I as defined above as a herbicidal agent. The invention also provides a herbicidal composition comprising one or more compounds of formula I as defined above in admixture with one or more substances selected from solvents, diluents and carriers. The invention further provides a method of treating plants, especially crops, for example, monocotyledenous plants, which comprises applying to the plants a compound of formula I as defined above, generally in the form of a herbicidal composition as defined above.

Compounds of formulae Ic and II are also part of the present invention.

The present invention also provides compounds of formula I as defined above with the exception of those compounds in which (i) R represents a methyl-substituted phenyl group, $R^1$ represents a methyl or ethyl group, and $R^2$ represents an amino group, and those in which (ii) R and $R^2$ both represent methylphenoxy groups and $R^1$ represents a methyl group. The present invention provides, for example, those compounds of formula I in which $R^2$ represents a group $NHR^3$ in which $R^3$ represents an aromatic or non-aromatic heterocyclic group having from 5 to 8 ring members and 1 or 2 heteroatoms, which may be the same or different, selected from oxygen, nitrogen and sulphur atoms, and optionally having an alkyl group having from 1 to 4 carbon atoms as a substituent on a ring nitrogen atoms, for example, as described further above.

The following Examples illustrate the invention, but are not limiting.

EXAMPLE 1

Tetra (2-nitrophenyl)-bisimidocarbonate sulphoxide 24.2 g of di(2-nitrophenyl) imidocarbonate was dissolved in 200 ml of dichloromethane containing 8.8 g of triethylamine, and the solution cooled to 5° C. in an ice bath. 4.76 g of thionyl chloride was dissolved in 50 ml of dichloromethane and added dropwise to the stirred imidocarbonate solution over a period of 30 minutes. Ice cooling was discontinued and the reaction solution stirred an additional 60 minutes before washing 3 times with water, drying over magnesium sulphate, and evaporating in vacuo to obtain the title compound as a crystalline solid. Recrystallisation from dichloromethane/toluene gave 20.2 g of the title compound, m.p. 179°–180° C.

$C_{26}H_{16}N_6SO_{13}$ requires: C 47.85, H 2.47, N 12.88; found: C 47.87, H 2.56, N 12.80.

EXAMPLE 2

Tetra (2-nitrophenyl)-bisimidocarbonate sulphone 19.6 g of tetra (2-nitrophenyl)-bisimidocarbonate sulphoxide was dissolved in 150 ml of dichloromethane and cooled to 5° C. with an ice bath. 8 g of meta-chloroperoxybenzoic acid dissolved in 100 ml of dichloromethane was added dropwise to the stirred sulphoxide solution. When addition was complete, the reaction mixture was stirred for 60 minutes before filtering off the crystalline product, which was then washed thoroughly with ether and dried to give 16.1 g of the title compound, m.p. 200°–203° C.

A second crop of 2.9 g of the title compound was obtained by washing the dichloromethane mother liquors with an aqueous sodium bicarbonate solution, drying over magnesium sulphate, and evaporating in vacuo. A sample recrystallised from chloroform/ether melted sharply at 203° C.

$C_{26}H_{16}N_6SO_{14}$ requires: C 46.71, H 2.41, N 12.57; found: C 46.63, H 2.50, N 12.59.

EXAMPLE 3

Tetra (4-methylphenyl)-bisimidocarbonate sulphoxide 43.2 g of p-cresol and 18 g of sodium hydroxide were dissolved in 800 ml of water and cooled to 5° C. in an ice bath. The mixture was stirred well, and 21.2 g of cyanogen bromide was added portionwise over a period of about 30 minutes. Ice cooling was then discontinued, and the reaction mixture was stirred for a further 60 minutes before filtering off the imidocarbonate, which was then washed thoroughly with water. The moist product was then dissolved in 300 ml of dichloromethane and dried over magnesium sulphate for one hour at 20° C. The filtered dichloromethane solution was then cooled to −40° C. and 13.6 g of triethylamine added. 7.32 g of thionyl chloride was then added to the stirred dichloromethane solution at a rate sufficient to maintain the reaction at −40° C. with continued cooling. When the addition was complete, the solution was allowed to come to ambient temperature and was then washed three times with water, dried over magnesium sulphate, and evaporated in vacuo. 21 g of the title compound was crystallised from ether, m.p. 130°–145° C. A sample recrystallised from ether had a melting point of 135° to 143° C. with decomposition.

$C_{30}H_{28}N_2SO_5$ requires: C 68.16, H 5.34, N 5.30; found: C 68.10, H 5.38, N 5.26.

EXAMPLE 4

Tetra (4-methylphenyl)-bisimidocarbonate sulphone 21 g of tetra (4-methylphenyl)-bisimidocarbonate sulphoxide was dissolved in 100 ml of dichloromethane and cooled to 5° C. with an ice bath. 8 g of meta-chloroperoxybenzoic acid dissolved in 100 ml of dichloromethane was added dropwise to the stirred sulphoxide solution. When the addition was complete, the reaction mixture was stirred for a further 60 minutes and then washed twice with a 5% aqueous sodium bicarbonate solution, dried over magnesium sulphate, and evaporated in vacuo. The residual crystalline solid was recrystallised from dichloromethane/ether to give 19.9 g of the title compound, m.p. 188°–190° C. A recrystallised sample melted at 193°–194° C.

$C_{30}H_{28}N_2SO_6$ requires: C 66.16, H 5.18, N 5.14; found: C 66.07, H 5.22, N 5.12.

EXAMPLE 5

4-Methyl-3,5-di(4-methylphenoxy)-1,2,4,6-thiatriazine 1,1-dioxide 1.088 g of tetra (4-methylphenyl)-bisimidocarbonate sulphone was suspended in 30 ml of acetonitrile. This solution was stirred well, and to it was added, at 20° C., 62 mg of methylamine. The clear solution which formed immediately after the addition of the amine was heated to reflux for 16 hours, then evaporated in vacuo to yield the title compound as a crystalline solid, which was recrystallised from acetonitrile/ether to give 592 mg of the title compound, m.p. 282°–286° C. Further recrystallisation gave a sample having a melting point of 290°–291° C.

$^1$H n.m.r. (250 MHz) DMSO-$d_6$ δ:2.34 (6H, s), 3.35 (3H, s), 7.25 (8H, ABq).

EXAMPLE 6

4-Ethyl-3,5-di(4-methylphenoxy)-1,2,4,6-thiatriazine 1,1-dioxide

By a proceedure analogous to that described in Example 5, but using ethylamine instead of methylamine, 430 g of the title compound was obtained, m.p. 302°–304° C. after recrystallisation from ethanol.

$^1$H n.m.r. (250MHz) DMSO-$d_6$ δ:1.45 (3H, t), 2.34 (6H, s), 4.22 (2H, q), 7.27 (8H, ABq).

EXAMPLE 7

4-Propargyl-3,5-di(4-methylphenoxy)-1,2,4,6-thiatriazine 1,1-dioxide

By a proceedure analogous to that described in Example 5, but using propargylamine instead of methylamnine, 495 g of the title compound was obtained, m.p. 279°–280° C. after recrystallisation from ethanol.

$^1$H n.m.r. (250 MHz) DMSO-$d_6$ δ:2.35 (6H, s), 3.31 (b 1H, s), 5.05 (2H, d), 7.27 (8H, ABq).

EXAMPLE 8

4-Isopropyl-3,5-di(2-nitrophenoxy)-1,2,4,6-thiatriazine 1,1-dioxide 2.68 g of tetra (2-nitrophenyl)-bisimidocarbonate sulphone was suspended in 100 ml of acetonitrile, and 236 mg of isopropylamine added dropwise to the stirred suspension at 20° C. The resulting clear orange solution was stirred for one hour at 20° C. and then concentrated to a volume of 20 ml in vacuo. The crystalline product was filtered off and recrystallised from acetonitrile to give 890 mg of the title compound, m.p. 259°–263° C. with decomposition.

$^1$H n.m.r. (250 MHz) DMSO-$d_6$ δ:1.67, (6H, d), 5.37 (1H, m), 7.67–8.34 (8H, m).

EXAMPLE 9

4-Isopropyl-3-methylamino-5-(2-nitrophenoxy)-1,2,4,6-thiatriazine 1,1-dioxide 450 mg of 4-isopropyl-3,5-di(4-nitrophenoxy)-1,2,4,6-thiatriazine 1,1-dioxide was suspended in 20 ml of acetonitrile and 32 mg of methylamine was added to the stirred solution at 20° C. The reaction mixture was stirred at 20° C. for 16 hours and the solvent evaporated in vacuo to yield a crystalline residue, which was chromatographed on silica gel using chloroform/acetonitrile as eluant. 162 mg of the title compound was obtained after recrystallisation from ethanol, m.p. 242° C. $^1$H n.m.r. (250 MHz) DMSO-d$_6$:1.54 (6H, d), 2.80 (3H, s), 4.61 (1H, m), 7.62–8.28 (4H, m), 8.06 (1H, br.s).

EXAMPLE 10

7-(2-Nitrophenoxy)-imidazolidinyl[1,2-c][1,2,4,6]-thiatriazine 5,5-dioxide 1.43 g of tetra (2-nitrophenoxy)-bisimidocarbonate sulphone was suspended in 25 ml of acetonitrile and 120 mg of 1,2-diaminoethane added to the stirred suspension at 20° C. After stirring at this temperature for 16 hours, the resulting fine crystalline solid was collected by filtration, washed thoroughly with ether, and dried in vacuo to give 506 mg of the title compound, m.p. 325° C. with decomposition.

$^1$H n.m.r. (250 MHz) DMSO-d$_6$ δ:3.67 (2H, m) 4.24 (2H, m), 7.63–8.28 (4H, m), 8.98 (1H, br.s).

We claim:

1. A compound of formula II

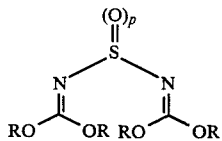
(II)

in which

R represents phenyl which is unsubstituted or substituted by one or two substituents, which is the same or different, selected from methyl, trifluoromethyl, nitro and cyano groups, and chlorine, fluorine and bromine atoms, and p represents the integer 1.

2. A process for the production of a compound of formula II

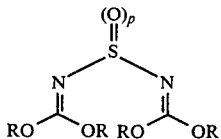
(II)

in which

R represents phenyl which is unsubstituted or substituted by one or two substituents, which is the same or different, selected from methyl, trifluoromethyl, nitro and cyano groups, and chlorine, fluorine and bromine atoms, and p represents the integer 1, which comprises reacting a compound of formula VI

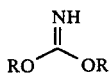
(VI)

in which R is as defined above, with thionyl chloride in the presence of an organic base.

3. A process as claimed in claim 2 wherein the base is a trialkylamine.

* * * * *